United States Patent [19]

Poindexter

[11] Patent Number: 5,288,925
[45] Date of Patent: Feb. 22, 1994

[54] METHOD FOR INHIBITING THE DEPOSITION OF ETHYLENE-VINYL ALCOHOL COPOLYMER

[75] Inventor: Michael K. Poindexter, Sugar Land, Tex.

[73] Assignee: Nalco Chemical Company, Naperville, Ill.

[21] Appl. No.: 983,202

[22] Filed: Nov. 30, 1992

Related U.S. Application Data

[63] Continuation-in-part of Ser. No. 822,255, Jan. 17, 1992, abandoned.

[51] Int. Cl.$^5$ .................. C07C 29/94; C07C 27/26
[52] U.S. Cl. ........................... 568/701; 568/840
[58] Field of Search ............ 568/913, 849, 854, 856, 568/868, 840, 701

[56] References Cited

U.S. PATENT DOCUMENTS

| | | | |
|---|---|---|---|
| 3,770,798 | 11/1973 | Norton | 260/465.5 |
| 3,853,810 | 12/1974 | Plank | 260/45.75 |
| 4,309,525 | 1/1982 | Nakabayashi et al. | 528/487 |
| 4,710,275 | 12/1987 | Berg et al. | 568/913 |
| 5,110,997 | 5/1992 | Dickakian | 570/222 |

Primary Examiner—Werren B. Lone
Attorney, Agent, or Firm—Robert A. Miller; Joseph B. Barrett; James J. Drake

[57] ABSTRACT

A method for preventing the precipitation of ethylene-vinyl alcohol copolymers in a distillation vessel. The vessel contains water, methanol, and ethylene-vinyl alcohol copolymers. The method includes the step of adding to the distillation vessel from 1 to about 1,000 ppm of at least one surfactant selected from the group consisting of alkyl, aryl, alkylaryl and arylalkyl sulfonic acids having a carbon length of from 4 to about 30 carbons. Preferably, the surfactant is dodecylbenzenesulfonic acid.

5 Claims, No Drawings

METHOD FOR INHIBITING THE DEPOSITION OF ETHYLENE-VINYL ALCOHOL COPOLYMER

This application is a continuation-in-part of co-pending patent application, Ser. No. 07/822,255, filed Jan. 17, 1992, now abandoned.

BACKGROUND OF THE INVENTION

Ethylene-vinyl acetate (EVA) copolymers are commercially important thermoplastic materials produced from ethylene and vinyl acetate. Transformation of EVA copolymers to other macromolecules can be readily achieved due to the potentially reactive acetoxy functionality. One of the most important transformations involves conversion of EVA copolymers to ethylene-vinyl alcohol (EVAL) copolymers. This transformation can go to completion or partial completion where the final product has both acetoxy and hydroxy moieties. As expected, such products possess needed properties different from their EVA copolymer precursors.

The transformation is typically accomplished by hydrolysis (reaction with water) or alcoholysis (reaction with an alcohol which is generally low boiling, e.g. methanol or ethanol). Furthermore, the reaction rate is enhanced greatly by the addition of a catalyst. Base catalysts are more preferred over acid catalysts. Many industrial processes use aqueous solutions of methanol and an alkaline catalyst (e.g. NaOH, KOH, NaOMe, LiOE+, etc.). The extent of the transformation is dictated by the process conditions.

After removal of the desired polymer, the alcohol used in the process is purified for reuse. The purification involves distilling the alcohol from the water and other components which have boiling points higher than the alcohol. This mixture also contains residual EVAL polymer which has a low water solubility. The removal of the alcohol results in the precipitation of the polymers in the distillation vessel. This is referred to as fouling. The precipitated EVAL polymer hinders the performance of the separation vessel and eventually the manufacturing process must be stopped to remove the precipitated polymer. Shutting down the manufacturing process to remove precipitated polymer is expensive and is preferably avoided. Accordingly, it would be advantageous to provide a method for preventing the precipitation of EVAL polymer in distillation vessels.

SUMMARY OF THE INVENTION

The invention provides a method for preventing the precipitation of ethylene-vinyl alcohol copolymers in a distillation vessel. The method includes the step of adding to the distillation vessel from 1 to about 1,000 ppm of at least one surfactant selected from the group consisting of C4 to C30 alkyl sulfonic acids, C6 to C30 aryl sulfonic acids, C7 to C30 alkyl substituted aryl sulfonic acids, and C7 to C30 aryl substituted alkyl sulfonic acids.

DESCRIPTION OF THE PREFERRED EMBODIMENTS

The present invention provides a method for preventing the precipitation of EVAL polymer in a distillation vessel. It has been surprisingly discovered that the addition of the surfactants of the invention to a distillation vessel including methanol, water, and ethylene-vinyl alcohol (EVAL) copolymer will prevent the precipitation of EVAL copolymer in the lower portion of the vessel during the removal of the methanol. Accumulation of solid EVAL copolymer results in shutting the column down for clean-out.

According to one embodiment of the invention, the surfactant is dodecylbenzenesulfonic acid, DDBSA. According to the invention, the DDBSA is diluted in a mixture of water and low molecular weight alcohols, preferably isopropyl alcohol and isobutyl alcohol, and is injected into the distillation vessel.

For purposes of the invention, the surfactant of the invention is at least one surfactant selected from the group consisting of C4 to C30 alkyl sulfonic acids, C6 to C30 aryl sulfonic acids, C7 to C30 alkyl substituted aryl sulfonic acids, and C7 to C30 aryl substituted alkyl sulfonic acids. It is believed that the alkali salts of these materials could be expected to function in the present invention. The dosage range of the surfactants is from 1 to about 1000 ppm, more preferably, the dosage range is from 10–100 ppm. Most preferably, the range is from 35–50 ppm.

The following example is presented to describe preferred embodiments and utilities of the invention and is not meant to limit the invention unless otherwise stated in the claims appended hereto.

EXAMPLE 1

Studies were performed on solid material (i.e. an EVAL copolymer) taken at a commercial manufacturing plant just before a distillation tower used to remove methanol overhead from water. Residual polymer which had accumulated just upstream of the distillation tower was received for testing. The solid was completely insoluble in water, but quite soluble in methanol (5% by weight). The material in methanol precipitated after sitting at room temperature for about one hour.

To simulate the precipitation, 1 milliliter aliquots of a 5% by weight solution of the EVAL copolymer in methanol were added to water (5ml) containing various chemical additives. Each sample was shaken and left to sit undisturbed at room temperature for two hours. The 5 milliliter of water was sufficient to effect the precipitation of the EVAL copolymer.

Solids resulting from the test were collected on tared filter paper and dried at 220° F. for 30 minutes. Each precipitated polymer weight was determined and compared to the weight of precipitate obtained when no additive (blank) was used. Results for dodecylbenzenesulfonic acid are shown in Table 1.

TABLE 1

| DOSAGE (μL)[a] | WT. OF FILTERED SOLID (mg) | % DISPERSED |
|---|---|---|
| Blank | 10.0 | 0 |
| 50 | 2.6 | 74 |
| 100 | 0.1 | 99 |
| 200 | 0.0 | 100 |
| 500 | 0.0 | 100 |

[a]Volume of docecylbenzenesulfonic acid in microliters.
% Dispersed = [(weight of polymer formed with no additive − weight of polymer formed with an additive)/weight of polymer formed with no additive] × 100%.

This test procedure represents a worse case scenario as the industrial unit functions at both higher temperature and tremendous agitation, both these factors would help keep the solids flowing more than the static, room temperature, lab test discussed above.

Changes can be made in the composition, operation and arrangement of the method of the present invention described herein without departing from the concept and scope of the invention as defined in the following claims.

I claim:

1. A method for preventing the precipitation of ethylene-vinyl alcohol copolymers in a distillation vessel, the vessel containing water, methanol, and ethylene-vinyl alcohol copolymers, the method including the step of adding to the distillation vessel from 1 to about 1,000 ppm of at least one surfactant selected from the group consisting of C4 to C30 alkyl sulfonic acids, C6 to C30 aryl sulfonic acids, C7 to C30 alkyl substituted aryl sulfonic acids, and C7 to C30 aryl substituted alkyl sulfonic acids.

2. The method of claim 1 wherein the surfactant is dodecylbenzene sulfonic acid.

3. The method of claim 1 wherein the surfactant is added in a dosage of from 10 to about 100 parts per million.

4. The method of claim 1 wherein the surfactant is added in a dosage of from about 35 to about 50 parts per million.

5. The method of claim 1, wherein the surfactant is a C7 to C30 alkyl substituted aryl sulfonic acid.

* * * * *